US008727948B2

(12) United States Patent
Herranen

(10) Patent No.: US 8,727,948 B2
(45) Date of Patent: May 20, 2014

(54) EXERCISE METHOD AND SYSTEM

(75) Inventor: Jouni Herranen, Oulunsalo (FI)

(73) Assignee: Healthy Exercise Holding Oy, Oulu (FI)

( * ) Notice: Subject to any disclaimer, the term of this patent is extended or adjusted under 35 U.S.C. 154(b) by 830 days.

(21) Appl. No.: 12/988,409

(22) PCT Filed: Apr. 20, 2009

(86) PCT No.: PCT/FI2009/050291
§ 371 (c)(1),
(2), (4) Date: Jan. 5, 2011

(87) PCT Pub. No.: WO2009/127788
PCT Pub. Date: Oct. 22, 2009

(65) Prior Publication Data
US 2011/0105279 A1 May 5, 2011

(30) Foreign Application Priority Data

Apr. 18, 2008 (FI) ..................................... 20085334

(51) Int. Cl.
*A63B 24/00* (2006.01)
(52) U.S. Cl.
USPC ................. 482/8; 482/1; 482/4; 482/901
(58) Field of Classification Search
USPC ................ 482/1–9, 900–902; 463/9; 700/91; 434/247
See application file for complete search history.

(56) References Cited

U.S. PATENT DOCUMENTS

| 4,828,257 | A | 5/1989 | Dyer et al. | |
|---|---|---|---|---|
| 5,706,822 | A | 1/1998 | Khavari | |
| 6,991,586 | B2 | 1/2006 | Lapcevic | |
| 7,507,183 | B2 * | 3/2009 | Anderson et al. | 482/1 |
| 7,713,171 | B1 * | 5/2010 | Hickman | 482/4 |
| 7,938,752 | B1 * | 5/2011 | Wang | 482/4 |
| 7,953,613 | B2 * | 5/2011 | Gizewski | 705/3 |
| 7,980,996 | B2 * | 7/2011 | Hickman | 482/1 |
| 2002/0128119 | A1 | 9/2002 | Arai | |
| 2004/0010420 | A1 | 1/2004 | Rooks | |
| 2004/0077462 | A1 | 4/2004 | Brown | |
| 2007/0033069 | A1 | 2/2007 | Rao | |
| 2007/0219059 | A1 | 9/2007 | Schwartz | |
| 2007/0225118 | A1 | 9/2007 | Giorno | |
| 2007/0287928 | A1 | 12/2007 | Kiviniemi et al. | |
| 2008/0171584 | A1 * | 7/2008 | Roberts et al. | 463/9 |
| 2010/0222178 | A1 * | 9/2010 | Shea | 482/4 |

OTHER PUBLICATIONS

International Search Report, dated Jul. 28, 2009, from corresponding PCT application.
European Search Report issued Dec. 13, 2013; European Patent Application No. 09732928.8.

* cited by examiner

*Primary Examiner* — Glenn Richman
(74) *Attorney, Agent, or Firm* — Young & Thompson

(57) ABSTRACT

The present invention provides a method for creating an exercise history for an exerciser to create an exercise program substantially in real-time, wherein personal exercise information is gathered to create the exercise history during an exercise event in an exercise environment having one or more exercise units. The present invention provides a method for creating an exercise program and a method for controlling an exercise event. The present invention also provides a device arrangement and a device which are arranged to perform the method of the invention.

20 Claims, 2 Drawing Sheets

EXERCISE METHOD AND SYSTEM

FIELD OF THE INVENTION

The present invention relates to a method for creating an exercise history for an exerciser and a method for creating an exercise program. More particularly the present invention relates to a method wherein personal exercise information is gathered automatically to create the exercise history. The present invention also relates to a device and device arrangement arranged to perform the methods of the invention.

BACKGROUND OF THE INVENTION

The exercise environments of today, like gyms and health clubs, are becoming more computerized. The equipment may provide ready user-selectable programs. In some systems computers are combined with exercise equipment and the identities of the exercisers are recognized. Also, some smart gym technologies allow training programs to be associated with user identities. The users can then identify themselves to exercise equipment with a unique key, such as a pin code, and the system will provide the preset training program to the user for that exercise equipment.

For example U.S. Pat. No. 6,991,586 discloses a system of simultaneously capturing data from multiple sources while individuals train on exercise equipment and using a wireless means of either transferring such data to a computer server for permanent storage and interactive analysis or prompt the delivery of programming content or data from a computer server to the exercise units or attachments affixed thereto.

Generally gyms and health clubs provide personal guidance for exercisers who want to start exercising with a new program, such as people who are not familiar with exercising methods and programs. This is done by a professional, such as a personal trainer or a physical therapist, who gathers information from the exerciser and possibly makes a personal estimate about the general fitness level, health and the like of the exerciser. The information may contain factors such as sex, age, weight, general physical activity, limiting factors (e.g. injuries), desired focus of the exercise and the general exercising history, which may also be none. By using this information the professional will prepare a personalized exercise program for the exerciser wherein the type of exercise, the level of exercise, number of series and repetitions to do, and the like are defined.

However, in some health clubs and gyms such professionals are not available. Examples of such exercise environments are health clubs or gyms at hotels, spas, old-age homes etc, wherein a little or no skilled personnel are available. For a person who would like to start exercising in such environment, a personal exercising program is desired.

It is the aim of the present invention to provide a method and system wherein a reliable personal training program can be created automatically for an exerciser without the help of a professional, such as a personal trainer or a physical therapist.

SUMMARY OF THE INVENTION

The present invention provides a method for creating an exercise history for an exerciser to create an exercise program, wherein personal exercise information is gathered to create the exercise history during an exercise event in an exercise environment having one or more exercise units which identify the exerciser currently exercising on a unit and gather personal exercise performance information and optionally physical information for said exerciser on each unit, and the exercise history is created preferably substantially in real-time based on this information. The present invention also provides a method for creating an exercise program, preferably substantially in real-time, based on said exercise history.

The present invention also provides a method for controlling an exercise event, wherein the method of the invention is used to create a new program or to change the current program preferably substantially in real-time during the exercise.

The present invention provides also a device for creating an exercise history for an exerciser to create an exercise program, wherein personal exercise information is arranged to be gathered to create said exercise history from an exercise environment having one or more exercise units comprising means for identifying the exerciser currently exercising on a unit, means for gathering personal exercise performance information and optionally physical information for said exerciser on each unit, and means for transferring said information to said device having a data processing and storage system, wherein the device is arranged to gather the information for creating the exercise history for said exerciser during an exercise event and to create the exercise history preferably substantially in real-time based on said information.

The device generally contains a data processing system and storage system to storage and process the gathered data and to control the exercise unit(s). Said device may be a separate unit containing one or more computer(s), or it may be integrated in an exercising unit. It may also be a computer, such as a server acting as a central processing system.

The present invention provides also a device arrangement for creating an exercise history for an exerciser to create an exercise program, wherein personal exercise information is arranged to be gathered to create said exercise history in an exercise environment having one or more exercise units, comprising means for identifying the exerciser currently exercising on a unit, means for gathering personal exercise performance information and optionally physical information for said exerciser on each unit, and means for transferring said information to a data processing and storage system, wherein the device arrangement is arranged to gather the information for creating the exercise history for said exerciser during an exercise event and to create the exercise history preferably substantially in real-time based on said information.

The device and the device arrangement are arranged to carry out any of the methods of the present invention.

The methods, devices and device arrangements of the invention are characterized by what is described in the independent claims. Some embodiments of the invention are described in the dependent claims.

One advantage of the present invention is that a personal exercise history can be created substantially automatically for the exerciser without the help of a skilled person or a professional.

Another advantage of the present invention is that a personal exercise program can be created substantially automatically for the exerciser without the help of a skilled person or a professional. Further, the program may be implemented or changed in real-time.

Still another advantage of the present invention is that the information to create the personal exercise history is gathered during a normal exercise event which aims for enhancing physical fitness. Because of this the exercise history contains exact information i.e. it is created in a real situation, and as new information is gathered during every exercise, it is always reliable and up to date.

DETAILED DESCRIPTION OF THE INVENTION

Figure 1:
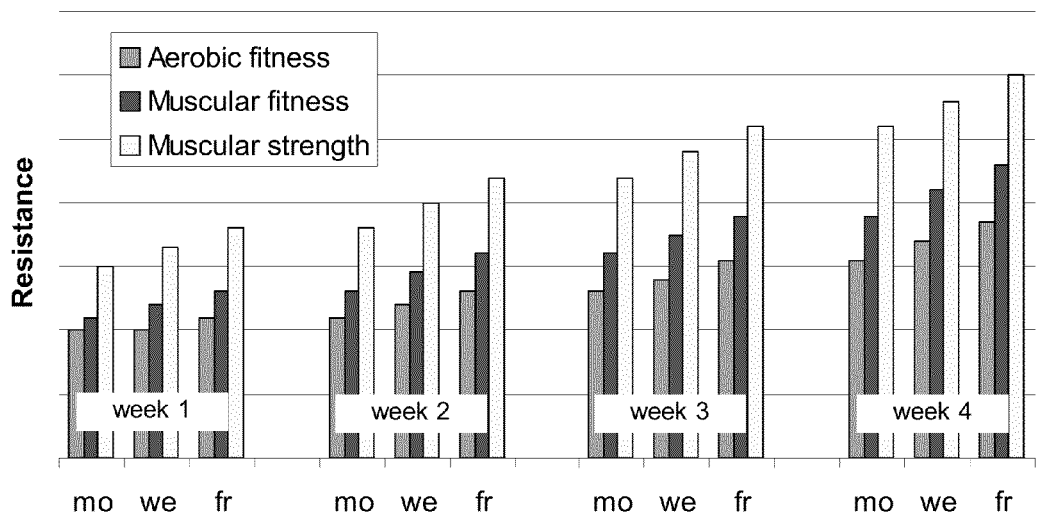
FIG. 1 shows the progression of the different steps in terms of resistance.

The present invention provides a method, device and device arrangement for creating an exercise history for an exerciser to create an exercise program. One embodiment of the present invention also provides a method for controlling an exercise event, wherein the said exercise history is used to create a new program or change the current program substantially in real-time during the exercise. In the state of the art the program is prepared by a professional, such as a personal trainer, physical therapist or the like. Generally the exercise program is created by first gathering the exerciser's personal information. Such information may be exact or numeric information and for example an estimate about the general condition of the exerciser made by the professional. Said exact or numeric information refers to information which can be defined or measured substantially clearly, such as sex, age, weight, fat percentage, general physical activity, limiting factors (e.g. injuries) or the desired focus of the exercise.

Besides this exact information the general fitness is usually estimated by a test. In many cases this is done for example by a short pedaling test or sometimes by asking questions about the recent exercise activity. However, this may not give an accurate picture of the general condition of the exerciser and hardly any information about the exercise history. The term "exercise history" as used herein refers to information from the previous workouts done by the exerciser, such as the level of exercise, progress, strength, number of series or repetitions performed, personal physical parameters during the exercise or the like. If the exerciser is a beginner i.e. in practice exercising for the first time, the exercise history may refer to the exercise starting level.

In the present invention personal exercise information is gathered to create the exercise history during a regular exercise event aiming for enhancing physical fitness in an exercise environment. To get exact measurable information the exercise environment contains one or more exercise units which identify the exerciser currently exercising on a unit and gather personal exercise performance information and optionally physical information for said exerciser on each unit, and the exercise history is created based on this information. In other words, the existing information i.e. old exercise history and the exerciser's personal information is combined with fresh personal exercise information to obtain a new exercise history and to create a new exercise program. This may be done substantially in real-time and the exercise units may be controlled and adjusted accordingly in real-time. "Real-time" or "substantially real-time" as used herein means that the feedback, such as the change in the present exercise program, can affect the ongoing exercise series or it can be otherwise provided to the exerciser during the ongoing exercise series. For example the real-time change in the program can change the settings of the exercise unit during the ongoing workout, for example the resistance or the amount of repetitions can be changed in the middle of the exercise series.

Said exercise units are known in the art and generally they have means for measuring the exercise performance, such as repetitions done, workload used, strength used, and the like. The units may also be able to take user-related measures, such as weight, pulse, fat percentage or the like. The means, such as any suitable sensors, for monitoring, measuring and/or collecting such information are well known in the art. It is also essential for the automated method that the units can recognize or identify the exerciser from other exercisers in order to be able to identify the gathered information. This may be carried out by the exerciser by entering a identifying code, name or similar to the unit, or more automated means may be used, such as a personal smart card, such as a bar code card, magnetic card, chip card, remote-readable card or other means, fingerprint, any suitable rfid means or electronic keys or the like, which can be read or recognized by the units themselves or some other system controlling the exercise environment to identify the exerciser.

The exercising units are generally connected to a data processing system, which acts as a control system or unit for the exercise unit set-up, by any suitable means, such as using wired or wireless networks, or the user may carry means for collecting said gathered information and the information is transferred to the data processing system from said means. In one embodiment the data processing system is a central data processing system. Said means may be any of the personalized smart cards mentioned above, memory cards or sticks or the like. Examples of such exercise environment and units are disclosed e.g. in U.S. Pat. No. 6,991,586. The "exercise unit" as used herein refers to any suitable entity wherein the exerciser can perform a specific exercise event or series. Said units may be normal exercising equipment generally used in gyms and health clubs, such as a exercise cycle, a cross trainer, a treadmill, a rowing machine, different types of weight machines, such as leg, back, biceps, triceps or ab machines or the like. The exercise unit may also be a multifunctional unit having more than one exercise functions.

This personal exercise performance information that said units can collect may be any suitable information, such as the amount of repetitions done or measured strength during one exercise series on an exercise unit. They may also be able to collect personal physical information, such as heart rate (pulse), weight, blood pressure, body fat percentage or flexibility.

In one embodiment the information is transferred to a data processing and storage system, and said data processing system creates the exercise history for said exerciser based on this information. In another embodiment said exercise performance information is compared to earlier corresponding exercise performance information on the same unit for the same exerciser to create the exercise history for said exerciser. Any suitable number or combination of said exercise units may be used. In one embodiment the exercise history is created based on change or progress in repetitions, strength, heart rate i.e. change in pulse between different or separate exercises in the same exercise/unit, weight, blood pressure, body fat percentage, flexibility or combinations thereof.

In one embodiment the information is transferred to a data processing and storage system substantially in real-time and said data processing system automatically creates a new program or changes the current program during the exercise. The feedback may be provided to the exerciser, exercising unit or both. In one embodiment the data processing system controls and adjusts the exercise unit(s) to change the exercise performance, or the target thereof, during the exercise according to the new program or as a response to the current exercise. The exercise time or recovery time may be subject to the response, as well as any physiological properties, such as pulse, impedance, fat percentage, body weight or the like. The response may also be a safety precaution for over-exercising, for example if the exerciser's pulse is too high, especially for persons recovering from cardiac conditions or operations. In one embodiment when the exerciser's heart rate exceeds certain limit during the exercise, the current exercise series is ended or the resistance of the exercise unit is lowered to protect the exerciser's health. The response may also be an alert to a person being on duty, such as a physiotherapist, who can in such case quickly check the exerciser's condition. The response may also help to keep up certain pulse level, or certain pulse may define the amount of repetitions or resistance. The units may have means for changing the exercise performance and the data processing system can control said means. The means may change the resistance of the unit with any suitable means, such as pneumatic, magnetic or other mechanical means. Also the repetition frequency, number of repetitions or the course of movement may be changed. The units may have displays for displaying information or instructions about the exercise for example to set the desired pace of the exercise.

In one embodiment the exercise program aims for improving aerobic fitness. The term "aerobic fitness" as used herein refers to very well known general fitness wherein the use of oxygen in the body's metabolic or energy-generating process is emphasized.

In another embodiment the exercise program aims for improving muscular fitness. The term "muscular fitness" as used herein refers to muscular tone or muscular endurance, which may be defined for example as the ability of a muscle to contract repeatedly or continuously. This is achieved by exercising by combining resistance training with cardiovascular function.

In still another embodiment the exercise program aims for improving muscular strength. The term "muscular strength" as used herein refers generally to the ability to produce muscular force. All said terms mentioned herein are well-known to a person skilled in the art.

In still another embodiment the exercise program aims for improving functional fitness. The term "functional fitness" as used herein refers to specific exercise of core muscles i.e. supporting muscles and it is aiming to improve muscle balance and posture.

In one embodiment the exercise aims for improving muscle and body balance. This may be achieved by separating the limbs when exercising i.e. both limbs do their own separate exercise movement simultaneously, which may be performed both at the same time or by turns. Also the balance training may be emphasize by removing supports normally used in the exercises, such as backrest or the like so the exerciser has to concentrate on keeping the balance during the exercise. The balance exercise may be applied to any of the exercise modes described herein, but especially to functional fitness mode.

In one embodiment the exercise program circulates exercise periods for at least two of the following exercise modes: aerobic fitness, muscular fitness, muscular strength and functional fitness. For example the exercise program provides first an exercise period for aerobic fitness, wherein series, repetitions and resistance suitable for aerobic workout are defined. When certain time period has expired and/or the exerciser has gained certain progress, the exercise program provides another exercise period, for example for muscular strength, wherein series, repetitions and resistance suitable for muscular strength workout are defined. Generally when a certain progress in an exercise mode is achieved, a new period of a different exercise mode is provided to the exerciser. Said progress may refer for example to progress in the exercise, such as in strength or aerobic fitness, time, or any exerciser's physiological parameters, such as pulse, weight, fat percentage or the like. The progress may be thus defined by measurements from the exercise itself or by measurements from the exerciser. The adequate progress in the exercise may also be considered as achieved when the progress in e.g. the gain of strength starts to decrease. One reason for changing the exercise mode is to avoid such saturation in exerciser. When the exercise mode is changed, the exerciser may utilize an active rest phase wherein the different mode is started at relatively lower level and the exerciser will recover from the earlier exercise mode. By changing the exercise mode the maximal efficiency of exercise is ensured. In one embodiment the different exercise mode is started at a relatively lower level than the earlier mode.

When such an exercise mode is started again, which has already been provided before, the system may provide a program wherein the starting level of the exercise period is higher than last time. This is because the exerciser presumably has gained progress in said exercise mode. The length of one exercise period generally depends on the type of exercise or the focus of exercise, but it may be for example in the range of 3-8 weeks.

The program mode can also be changed during certain period. For example the exerciser may want to have a muscular strength exercise during an aerobic period. When such other mode is chosen the program will be automatically changed to said mode and updated to be at the right level (resistance, repetitions etc.).

The personalized exercise program of the present invention and the feedback related to it may be provided to the exerciser in any suitable way. For example the exercise units may first recognize the exerciser, show the program, target of the exercise or any other suitable information on a display and adjust the unit to provide to the exerciser suitable resistance for the present workout. The exercise unit may also monitor the workout and provide information on the progress thereof. Also physiological information, such as pulse, may be monitored and displayed. The exercisers may also get the program in any suitable other way.

The different exercises i.e. plurality of exercise units may be arranged as a circuit training style wherein after one exercise series on one unit the exerciser moves to another exercise unit for another series. Alternatively the exerciser may perform more than one series on the same unit before moving to another one. The display of the exercise unit may guide the exerciser to the next unit.

The exercise environment may be networked to other similar environments to provide a mobile exerciser the opportunity to exercise with the same program and exercise history for example while travelling. In such arrangement the user may be recognized from a central data base which can be accessed from any of such exercise environment. The information, such as the personal exercise history, is always up to date and can be utilized regardless of the place of exercise. Such system can be applied e.g. to health clubs, gyms, hotels or the like having a place of business in different cities.

Figure 2:
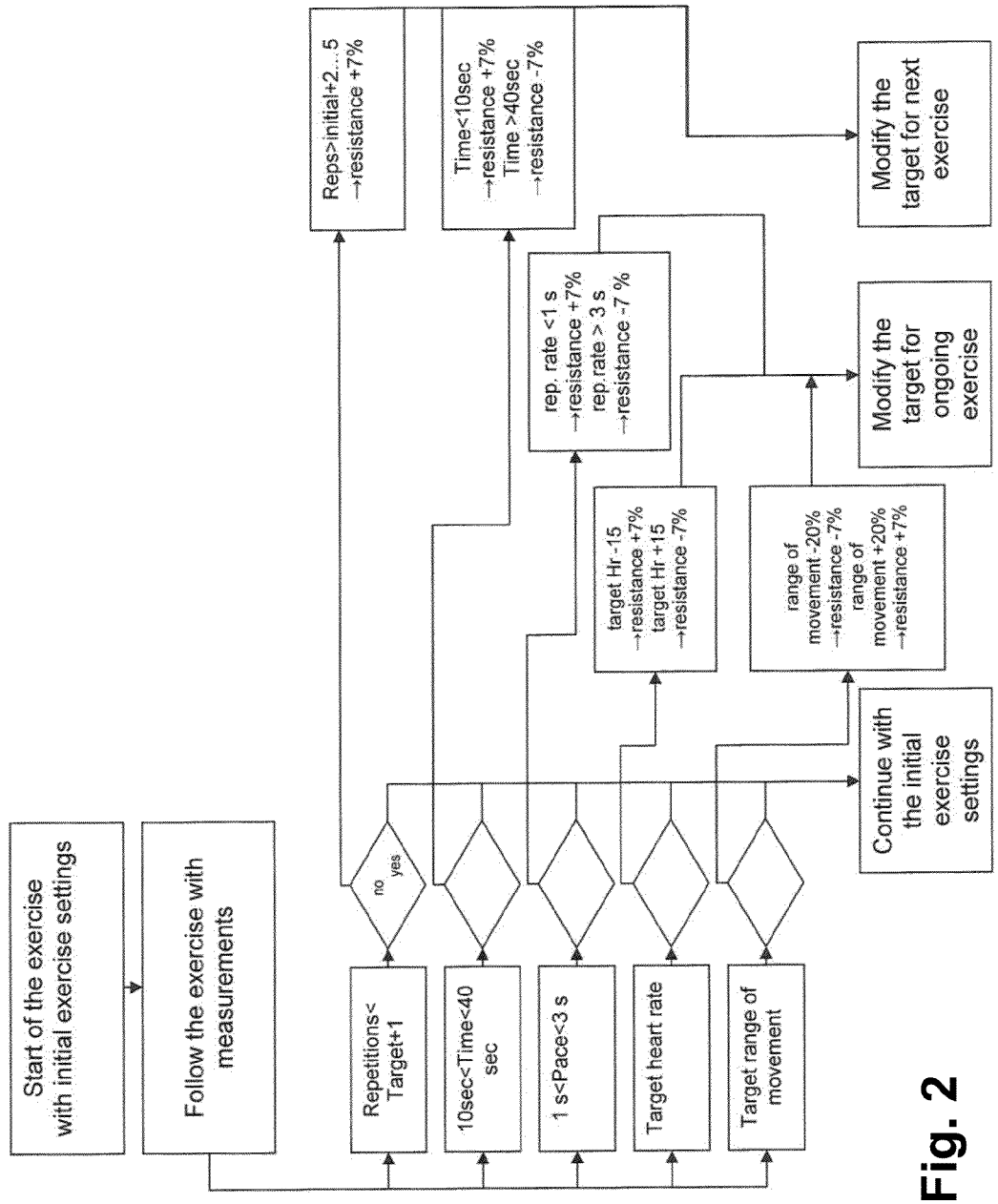
FIG. 2 shows a block diagram of an exemplary control of the exercise with the method of the invention.

The principle of the invention is presented in FIG. 2 as a non-limiting example. The exercise is started with initial exercise settings. During the exercise several measurements are carried out, such as the amount of repetitions, duration of the exercise, pace of the exercise, heart rate and the range of movement. Depending on the measured values the exerciser may either continue with the initial exercise settings if the values are in the pre-defined range, or the exercise program may be changed. For example if the repetition rate (pace) is below the predefined value 1 second, the resistance is increased by 7%. On the other hand, if the repetition rate is above 3 seconds (one repetition in 3 seconds), the resistance is decreased by 7%. The same may apply to the other parameters as well. Some measured values may affect the exercise immediately and the target for the ongoing exercise will be modified in real-time (for example pace, heart rate or range of movement). Some measured values may affect the next exercise, or they may affect both.

Now the present invention will be described with examples. These examples are provided only to enlighten the idea of the present invention and they should not be considered as limiting the scope of the invention. A person skilled in the art can find out several other embodiments which can be applied on different exercise environments, units and the like within the scope of the attached claims.

EXAMPLES

The following example describes one embodiment to carry out the method of the present invention as a 30-minute exercise concept wherein one series of each type of exercise is done during one 30-minute exercise session. This concept is based on the study conducted in the University of Glamorgan Health and Exercise Science Unit (School of Applied Sciences) wherein it was discovered that a similar improvement can be seen, in terms of muscle strength, by people who perform either one or three sets of upper body resistance training exercises. The training is carried out as circuit training including warm-up, resistance training and stretching. The program is always carried out in the same order, and it is fully guided from start to finish. The exercise equipment settings are adjusted with the exerciser's personal identifier, which includes the exerciser's ID information. The system transmits the exercise performance information between the exercise equipment and the information system automatically before and after the exercise.

The program begins with a 10-minute warm-up with an exercise bike or a cross-trainer. These alternatives have been chosen for the warm-up because they are safe, effective and easy to use. The purpose of the warm-up is to increase the heart-rate to the aerobic level and to warm up the muscles. The resistance training is carried out with twelve different fitness machines which train the leg muscles, stomach and back muscles, the rotators, upper body muscles, as well as the extensor and flexor muscles. The program ends with an eight-step stretching program at a stretching device. The stretching can then be boosted with stall bars, gym sticks and gym balls.

The training is based on a three-step program, where each cycle lasts for one month (four weeks). FIG. 1 illustrates the progression of the steps in terms of resistance. The figure shows how the resistance increases as the exerciser advances, and the next step always starts at a slightly lower level than where the previous step ended. In this example the following exercise modes are used.

Aerobic Stage (1 Month)

The purpose of this stage is to get the muscles used to resistance training and to improve the condition of the cardiovascular system. In the beginning, the resistance is very small, even too small. The system automatically increases the resistance as the exerciser progresses. The repetitions at this stage are 22 for each machine. If the exerciser does 24 repeats or more, the system automatically adds the resistance to the next workout.

Muscular Fitness Stage (1 Month)

The goal at this stage is to improve muscular endurance and muscle fitness. This stage, too, starts with resistance that is smaller than at the end of the previous stage and which the system automatically increases during the stage. The repetitions during this stage are 15 per machine. In case the exerciser does 17 repetitions or more, the system automatically increases the resistance next time.

Power Stage (1 Month)

The goal of this stage is to improve muscular strength. The program is based on moderate resistance and relatively high number of repetitions. The system automatically increases the resistance during the exercise. The repetitions at this stage are ten per machine. Should the exerciser do twelve or more repetitions, the system automatically increases the resistance in the next workout.

Next it is described how the different exercise programs may be prepared. In Table 1 the exercises used are listed as the basic program. The basic program will then be adjusted according to the type of exercise mode and the personal characteristics of the exerciser.

TABLE 1

Basic exercise (applied to cases wherein the relative percentage is "Basic")

| Unit No | Exercise | time | resistance | repetitions |
|---|---|---|---|---|
| 1 | Cardio (bike or Cross-trainer) | 10 min | | |
| 2 | Leg press | | X | 22 |
| 3 | Lower back | | x | 22 |
| 3 | Abs | | x | 22 |
| 4 | Twist L | | x | 22 |
| 4 | Twist R | | x | 22 |
| 5 | Chest curl | | x | 22 |
| 6 | Pull down | | x | 22 |
| 6 | Push up | | x | 22 |
| 7 | Biceps | | x | 22 |
| 7 | Triceps | | x | 22 |
| 8 | Stretch trainer | 5-8 min | | |

A simple question pattern such as shown in Table 2 is asked and a basic starting profile is created for the exerciser.

TABLE 2

| Question No | Question | Choise 1/ Effect | Choise 2/ Effect | Choise 3/ Effect | Choise 4/ Effect |
|---|---|---|---|---|---|
| 1 | Language | Finnish Basic | English Basic | | |
| 2 | Sex | Male Basic | Female 70% | | |
| 3 | Age | <30 Basic | 30-50 90% | 50-65 80% | >65 70% |
| 4 | Exercises per week | 0-1 75% | 2-3 90% | >3 Basic | |
| 5 | Limiting factors | Back | Knee | Shoulder | |
| | Unit 1 | | xxx | | |
| | Unit 2 | | xx | | |
| | Unit 3 | xx | | | |
| | Unit 4 | xx | | | |
| | Unit 5 | | | xx | |
| | Unit 6 | | | xx | |
| | Unit 7 | | | | |
| | Unit 8 | xx | | | |
| 6 | Exercise mode | Aerobic Basic | Muscle fitness 120% | Muscle strength 140% | |

For example based on question 3, the age of the exerciser, the resistance level may be adjusted to either basic level or to a lower level. In this case the basic exercise program is applied as such to exercisers under 30. The older the exerciser, the lower the resistance level. Further, the current exercise activity is enquired. If the exerciser has no or very little exercise activity (e.g. 0-1 times per week), a low-resistance program may be selected. An active exerciser may start with the basic program.

Further, any exercise-limiting factors are enquired. Any back, knee or shoulder injuries or conditions may lead to restriction in certain exercises. For example in case of back problems the resistance level in Unit 2 may be decreased 30% and in Unit 4 20%. Knee problems result in the use of bike only as the cardio exercise and 25-40% lower resistance level in Unit 2. In case of shoulder problems the push up exercise in Unit 6 will be done by 50% lower resistance level, Unit 5 by 25% lower and pull done exercise in Unit 6 by 20% lower level.

For exercisers over 65 the cardio exercise would always be bike, as well as for exercisers having no or very little other exercise activity.

To illustrate how the different personal exercise programs may be created, some examples are shown in the following tables 3-5.

TABLE 3

Personalized starting exercise program for male under 30 years currently exercising over three times per week

| Unit No | Male <30 Exercise | time | Aerobic fitness Resistance | Reps | Muscular fitness Resistance | Reps | Muscular strength Resistance | Reps |
|---|---|---|---|---|---|---|---|---|
| 1 | Cardio | 10 min | | | | | | |
| 2 | Leg press | | 90 | 22 | 100 | 15 | 110 | 10 |
| 3 | Lower back | | 30 | 22 | 32 | 15 | 34 | 10 |
| 3 | Abs | | 30 | 22 | 32 | 15 | 34 | 10 |
| 4 | Twist L | | 12 | 22 | 14 | 15 | 16 | 10 |
| 4 | Twist R | | 12 | 22 | 14 | 15 | 16 | 10 |
| 5 | Chest curl | | 12 | 22 | 13 | 15 | 14 | 10 |
| 6 | Pull down | | 23 | 22 | 24 | 15 | 25 | 10 |
| 6 | Push up | | 10 | 22 | 12 | 15 | 14 | 10 |
| 7 | Biceps | | 11 | 22 | 11 | 15 | 12 | 10 |
| 7 | Triceps | | 10 | 22 | 12 | 15 | 14 | 10 |
| 8 | Stretch trainer | 5-8 min | | | | | | |

TABLE 4

Personalized starting exercise program for male 50 years currently exercising 2 times per week

| Unit No | Male 50 Exercise | time | Aerobic fitness Resistance | Reps | Muscular fitness Resistance | Reps | Muscular strength Resistance | Reps |
|---|---|---|---|---|---|---|---|---|
| 1 | Cardio | 10 min | | | | | | |
| 2 | Leg press | | 55 | 22 | 60 | 15 | 65 | 10 |
| 3 | Lower back | | 24 | 22 | 26 | 15 | 28 | 10 |
| 3 | Abs | | 25 | 22 | 26 | 15 | 27 | 10 |
| 4 | Twist L | | 9 | 22 | 11 | 15 | 12 | 10 |
| 4 | Twist R | | 9 | 22 | 11 | 15 | 12 | 10 |
| 5 | Chest curl | | 6 | 22 | 8 | 15 | 10 | 10 |
| 6 | Pull down | | 16 | 22 | 18 | 15 | 20 | 10 |
| 6 | Push up | | 4 | 22 | 5 | 15 | 6 | 10 |
| 7 | Biceps | | 5 | 22 | 6 | 15 | 7 | 10 |
| 7 | Triceps | | 7 | 22 | 8 | 15 | 9 | 10 |
| 8 | Stretch trainer | 5-8 min | | | | | | |

TABLE 5

Personalized starting exercise program for female over 65 years currently exercising 0 times per week

| Unit No | Female >65 Exercise | time | Aerobic fitness Resistance | Reps | Muscular fitness Resistance | Reps | Muscular strength Resistance | Reps |
|---|---|---|---|---|---|---|---|---|
| 1 | Cardio | 10 min | | | | | | |
| 2 | Leg press | | 22 | 22 | 35 | 15 | 30 | 10 |
| 3 | Lower back | | 12 | 22 | 13 | 15 | 14 | 10 |
| 3 | Abs | | 15 | 22 | 16 | 15 | 17 | 10 |
| 4 | Twist L | | 4 | 22 | 5 | 15 | 5 | 10 |
| 4 | Twist R | | 4 | 22 | 5 | 15 | 5 | 10 |
| 5 | Chest curl | | 2 | 22 | 3 | 15 | 4 | 10 |
| 6 | Pull down | | 9 | 22 | 10 | 15 | 11 | 10 |
| 6 | Push up | | 1 | 22 | 1 | 15 | 2 | 10 |
| 7 | Biceps | | 2 | 22 | 2 | 15 | 3 | 10 |
| 7 | Triceps | | 3 | 22 | 4 | 15 | 4 | 10 |
| 8 | Stretch trainer | 5-8 min | | | | | | |

The invention claimed is:

1. A method for creating an exercise history for an exerciser to create an exercise program, said method comprising the steps of:
in an exercise environment having first and second exercise units, the exerciser performing exercise events with the first and second exercise units while the first and second exercise units are operatively connected to a computer data processing system with exercise performance information being transmitted between the first and second exercise units and the data processing system;
during said exercise events, the data processing system gathering information including i) an identification of the exerciser using one of the first exercise unit and the second exercise unit, and ii) personal exercise performance information of the exerciser;
the data processing system, using the gathered information from said gathering information step, creating an exercise history for the exerciser during a first exercise event;
the data processing system, substantially in real-time and based on said gathered information and said created exercise history, creating for the exerciser new exercise programs for each of different exercise modes aiming for improving at least two of the following: aerobic fitness, muscular fitness, muscular strength and functional fitness; and
the data processing system controlling and adjusting each of the exercise units to change an exercise target by changing the exercise performance of the exerciser during a current exercise event i) using one of the created new exercise programs in response to the exerciser changing exercise mode, or ii) as a response to the gathered personal exercise performance information of the exerciser from the current exercise event.

2. The method of claim 1, wherein, the data processing system, using the created new exercising programs, circulates exercise periods for at least two of the following exercise modes: aerobic fitness, muscular fitness, muscular strength and functional fitness.

3. The method of claim 1, wherein when a certain exercise performance progress in a certain exercise mode is achieved, the data processing system provides a new period of a different exercise mode.

4. The method of claim 3, wherein the data processing system starts the different exercise mode at a relatively lower exercise level than an ending exercise level of a different earlier exercise mode or of an ending exercise level of an earlier exercise time period with a same exercise mode.

5. The method of claim 1, wherein said gathered information is transferred to a data storage system of the data processing system for storage, and said data processing system creates the exercise history for said exerciser based on the stored information in addition to gathered information of the current exercise event.

6. The method of claim 1, wherein said gathered information is transferred to the data processing system substantially in real-time and said data processing system changes a current exercise program during the current exercise event.

7. The method of claim 1, wherein said exercise performance information includes an amount of repetitions done or measured strength during one exercise series on said exercise unit.

8. The method of claim 1, wherein said exercise performance information is compared to earlier corresponding exercise performance information on the same exercise unit for the same exerciser to create the exercise history for said exerciser.

9. The method of claim 1, wherein the exercise history is created based on change or progress in at least one of repetitions, strength, heart rate, weight, blood pressure, body fat percentage, and flexibility.

10. A method of claim 1, wherein the exercise history of previous exercise events of the exerciser stored on a data storage unit of the data processing systems is used to create said new exercise programs.

11. A method of claim 1, substantially in real-time during the current exercise event, in response to the exerciser changing the exercise mode to a new exercise mode, the data processing system controls and adjusts the first exercise unit to change the exercise target of the exerciser by changing the exercise performance of the exerciser using one of the created new exercise programs corresponding to the new exercise mode, the new exercise mode being one of aerobic fitness, muscular fitness, muscular strength, and functional fitness.

12. The method of claim 1, wherein when the exerciser's heart rate exceeds a certain limit during the current exercise event, the data processing system lowers a resistance of the first exercise unit.

13. The method of claim 1, wherein when the exerciser's heart rate exceeds a certain limit during the current exercise event, the data processing system controls the first exercise unit to end the current exercise event.

14. The method of claim 1,
wherein said step of gathering information further includes the data processing system gathering physical information for each of the exerciser on each of the first and second exercise units, and
wherein said physical information includes at least one of heart rate, weight, blood pressure, body fat percentage, and flexibility.

15. A device arrangement for creating an exercise history for an exerciser to create an exercise program, comprising:
an exercise environment having first and second exercise units operatively connected to a computer data processing and storage system and configured so that exercise performance information is transmitted between the first and second exercise units and the data processing and storage system during exercise events, wherein personal exercise performance information is arranged to be gathered by the data processing and storage system to create a exercise history for the exerciser using the first and second exercise units;
means for identifying the exerciser currently exercising on each said exercise unit;
means for gathering the personal exercise performance information for said exerciser on each exercising unit, and
means for transferring said gathered personal exercise performance information to the data processing and storage system,
wherein i) a storage unit of the data processing and storage system stores the exercise history for said exerciser during an exercise event and ii) the data processing and storage system creates the exercise history substantially in real-time based on said gathered personal exercise performance information to create new exercise programs for each of different exercise modes aiming for improving at least two of the following: aerobic fitness, muscular fitness, muscular strength and functional fitness.

16. The device arrangement of claim 15, wherein said data processing and storage system i) creates the exercise history for the exerciser based on the stored information in addition to the gathered personal exercise performance information of a current exercise event, and ii) in substantially real-time and based further on said stored exercise history, creates the new exercise programs for each of different exercise modes.

17. The device arrangement of claim 15, wherein the data processing system controls and adjusts each of the exercise units to change an exercise target by changing the exercise performance of the exerciser during a current exercise event i) using one of the created new exercise programs in response to the exerciser changing exercise mode, or ii) as a response to the gathered personal exercise performance information of the exerciser from the current exercise event.

18. A device for creating an exercise history for an exerciser to create an exercise program, said device comprising:
a computer data processing and storage system operatively connected to an exercise environment having a plurality of exercise units, the exercise units comprising means for identifying the exerciser currently exercising on each exercise unit, means for gathering personal exercise performance information and physical information for said exerciser on each unit, and means for transferring said gathered information to said data processing and storage system,
wherein the data processing and storage system is configured to gather the personal exercise performance information for creating an exerciser-specific exercise history for said exerciser during each exercise event and to create the exercise history substantially in real-time based on said gathered information, the data processing and storage system configured to create new exercise programs for each of different exercise modes aiming for improving at least two of the following: aerobic fitness, muscular fitness, muscular strength and functional fitness.

19. The device of claim 18, wherein said data processing and storage system i) creates the exercise history for the exerciser based on the stored information in addition to the gathered personal exercise performance information of a current exercise event, and ii) in substantially real-time and based further on said stored exercise history, creates the new exercise programs for each of different exercise modes.

20. The device of claim 18, wherein the data processing system controls and adjusts each of the exercise units to change an exercise target by changing the exercise performance of the exerciser during a current exercise event i) using one of the created new exercise programs in response to the exerciser changing exercise mode, or ii) as a response to the gathered personal exercise performance information of the exerciser from the current exercise event.

* * * * *